United States Patent
Lipinski et al.

(10) Patent No.: US 9,220,927 B2
(45) Date of Patent: *Dec. 29, 2015

(54) HAIR DYEING COMPOSITION

(71) Applicant: KAO GERMANY GMBH, Darmstadt (DE)

(72) Inventors: Normen Lipinski, Frankfurt (DE); Michael Molenda, Frankfurt (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/369,389

(22) PCT Filed: Dec. 20, 2012

(86) PCT No.: PCT/EP2012/076485
§ 371 (c)(1),
(2) Date: Jun. 27, 2014

(87) PCT Pub. No.: WO2013/098211
PCT Pub. Date: Jul. 4, 2013

(65) Prior Publication Data
US 2014/0373865 A1    Dec. 25, 2014

(30) Foreign Application Priority Data
Dec. 29, 2011   (EP) ...................................... 11196098

(51) Int. Cl.
*A61Q 5/10* (2006.01)
*A61K 8/60* (2006.01)
*A61Q 5/06* (2006.01)

(52) U.S. Cl.
CPC ... *A61Q 5/10* (2013.01); *A61K 8/60* (2013.01); *A61K 8/604* (2013.01); *A61Q 5/065* (2013.01)

(58) Field of Classification Search
CPC .......... A61Q 5/10; A61Q 5/065; A61K 8/604
USPC ............................................................. 8/405
See application file for complete search history.

(56) References Cited

U.S. PATENT DOCUMENTS

2006/0260070 A1* 11/2006 Legrand ............................ 8/405
2011/0052518 A1* 3/2011 Pratt et al. ....................... 424/62

FOREIGN PATENT DOCUMENTS

WO   WO 2011/009562 A2 *  1/2011 ............... A61Q 5/10

* cited by examiner

*Primary Examiner* — Eisa Elhilo
(74) *Attorney, Agent, or Firm* — Norris McLaughlin & Marcus PA

(57) ABSTRACT

Present invention relates to a hair dyeing composition comprising an anionic sugar surfactant which delivers long lasting colouration to human hair. The object of the present invention is an aqueous hair dyeing composition comprising one or more hair direct dyes and at least one anionic sugar surfactant. Suitable and particularly preferred anionic sugar surfactant is lauryl glucose carboxylate and its alkali metal salts such as sodium and potassium.

14 Claims, No Drawings

HAIR DYEING COMPOSITION

This application is a 371 application of PCT/EP2012/076485 filed Dec. 20, 2012, which claims foreign priority benefit under 35 U.S.C. §119 of European Application No. 11196098.5 filed Dec. 29, 2011, the disclosures of which are all incorporated herein by reference.

Present invention relates to a hair dyeing composition comprising an anionic sugar surfactant which delivers long lasting colouration to human hair.

Lifetime of a hair colour has always been one of the important point in developing hair colour products and/or products to be used on artificially coloured hair. Especially the lifetime of colour achieved with a composition comprising hair solely direct dyes is always considered to be short. There have been many attempts to extend the lifetime of colour, but without a satisfactory result up until now.

The aim of the inventors of the present invention is to provide hair dyeing compositions comprising hair direct dyes which deliver hair color with considerable longer life time compared to the ones currently available.

The inventors of the present invention have surprisingly found out that a hair dyeing composition comprising one or more hair direct dyes and an anionic sugar surfactant has considerably longer lifetime than a composition based on hair direct dyes but not comprising anionic sugar surfactant.

Accordingly the first object of the present invention is an aqueous hair dyeing composition comprising one or more hair direct dyes and at least one anionic sugar surfactant.

The term sugar surfactant it is meant that the surfactant is derived from a monosaccharide such as a hexose for examples glucose, galactose and mannose.

Further object of the present invention is the use of an aqueous composition comprising one or more hair direct dyes and at least one anionic sugar surfactant for colouring hair.

Still further object of the present invention is a process for colouring hair wherein an aqueous composition comprising one or more hair direct dyes and at least one anionic sugar surfactant is applied onto hair and rinsed off from hair after processing 1 to 45 min.

Further object of the present invention is a kit for hair comprising one or more compositions wherein one of the compositions is an aqueous composition comprising one or more hair direct dyes and at least one anionic sugar surfactant.

Compositions of the present invention comprise one or more hair direct dyes. The direct dyes suitable are the ones generally known in the art such as anionic, cationic and non-ionic ones. Plant dyes are also suitable for the compositions of the present invention.

Suitable anionic direct dyes in aqueous composition are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27 and DC Yellow 10.

Suitable cationic dyes in aqueous composition are in principal those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87 and Basic Orange 31. The most preferred ones are Basic red 51, Basic Yellow 87 and Basic Orange 31 sold by CIBA.

Additionally, the aqueous compositions of the present invention comprise neutral dyes (HC dyes), so called nitro dyes. Some examples to those are: HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Plant dyestuffs can also be used alone or in combination with synthetic direct-acting dyestuffs, for example henna (red or black), alkanna root, laccaic acid, indigo, logwood powder, madder root and rhubarb powder, etc.

Further suitable direct dyes which are anionic under alkaline conditions are according to the following structures:

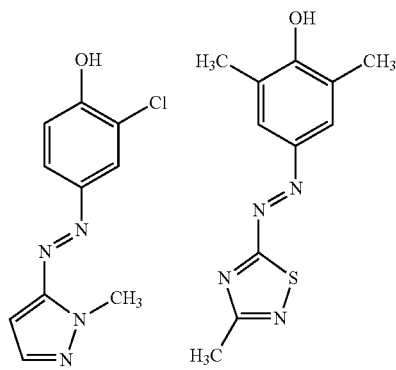

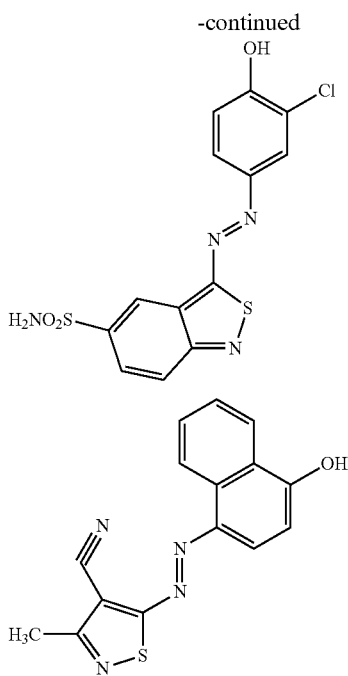

From the above disclosed direct dyes the preferred are cationic and nitro dyes.

According to the invention, the composition comprises one or more direct dye at a concentration of 0.01 to 10%, preferably 0.05 to 7.5% and more preferably 0.2 to 5% by weight calculated to the total composition. The composition can also comprise mixture of several direct dyes i.e. an anionic, a cationic and/or a nonionic ones. In such a case the dyes may be mixed at any ratio with each other.

Compositions of the present invention comprise at least one at least one anionic sugar surfactant. Suitable and particularly preferred anionic sugar surfactant is lauryl glucose carboxylate and its alkali metal salts such as sodium and potassium. Lauryl glucose carboxylate is carboxymethyl ether of lauryl glucoside. Sodium lauryl glucose carboxylate is available under the trade name Plantapon from Cognis.

Compositions comprises at least one sugar surfactant, in particular lauryl glucose carboxylate and its alkali metal salt at a concentration in the range of 0.1 to 25%, preferably 0.2 to 20 and more preferably 0.5 to 15 and most preferably 1 to 10% by weight calculated to the total composition.

Compositions of the present invention may be in the form of emulsion, solution, dispersion and/or gel. Emulsion is the preferred form.

In the case the composition is in the form of an emulsion, it comprises as an emulsion base at least one fatty alcohol or mixture of fatty alcohols with the chain length of 14 to 22 C atoms. Examples to suitable fatty alcohols, without limiting the choice, are myristyl alcohol, cetyl alcohol, stearyl alcohol, behenyl alcohol and cetostearyl alcohol. The most preferred is cetostearyl alcohol well known with its trade name Lanette 0 or as Lanette N in mixture with sodium cetearyl sulfate from Cognis.

The concentration of fatty alcohol(s) is in the range from 0.5 to 20%, preferably 1 to 15% by weight, calculated to total composition prior to mixing with oxidizing and bleaching and/or highlighting composition.

Compositions according to present invention may comprise surfactants selected from anionic, nonionic, amphoteric and cationic surfactants as emulsifier or solubilizer. Cationic surfactants are as well used as hair conditioners in the compositions.

Anionic surfactants suitable within the scope of the invention are in principal known from the cleansing compositions These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are a-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof as well as alkyl amido polyether carboxylic acids and salts thereof. Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

It is also possible to use mixtures of several anionic surfactants.

An overview of the anionic surfactants suitable for the present invention can furthermore be found in the monography of K. Schrader, "Grundlagen and Rezepturen der Kosmetika", $2^{nd}$ Ed.(1989, Hüthig Buchverlag), pp. 595-600 and pp. 683 to 691.

Further surfactants in the compositions according to the invention are nonionic surfactants alone or in admixture with anionic surfactants. These are described as well in Schrader, l.c., on pages 600-601 and pp. 694-695. Especially suited nonionic surfactants are, for example, long-chain fatty acid mono- and dialkanolamides, such as coco fatty acid mono- or diethanolamide and myristic fatty acid mono or diethanolamide, stearic acid mono or diethanolamide. Further nonionic surfactants suited are alkyl polyglucosides with an alkyl group of 8 to 18 carbon atoms, and with 1 to 5 glucoside units. Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics$^R$", as well as fatty alcohol ethoxylates.

Further nonionic surfactants preferred in the dyeing compositions according to invention are $C_{10}$-$C_{22}$-fatty alcohol ethoxylates. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 25, preferably about 10 and about 20.

As further surfactant component, the compositions according to the invention can also contain amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Composition can contain cationic surfactants as emulsifier, solubilizer and/or conditioning ingredients according to the formula $$R_6-\overset{\overset{R_3}{|}}{\underset{\underset{R_5}{|}}{N^+}}-R_4 \quad X^-$$

where $R_3$ is a saturated or unsaturated, branched or linear alkyl chain with 8-22 C atoms or $$R_7\,CO\,NH\,(CH_2)_n$$

where $R_7$ is saturated or unsaturated, branched or linear alkyl chain with 7-21 C atoms and n has typical value of 1-4 or $$R_8\,CO\,O(CH_2)_n$$

where $R_8$ is saturated or unsaturated, branched or linear alkyl chain with 7-21 C atoms and n has typical value of 1-4, and
$R_4$ is H or unsaturated or saturated, branched or linear alkyl chain with 1-22 C atoms or $$R_7\,CO\,NH\,(CH_2)_n$$

or $$R_8\,CO\,O(CH_2)_n$$

where $R_7$, $R_8$ and n are same as above.

$R_5$ and $R_6$ are H or lower alkyl chain with 1 to 4 Carbon atoms, and X is typically chloride, bromide, methosulfate.

Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethyl-monium methosulfate.

Concentration of one or more surfactants other than the sugar surfactant in dyeing composition is in the range of 0.1 to 20%, preferably 0.2 to 15% and most preferably 0.2-10% by weight, calculated to the total composition.

Further, compositions may comprise polymers selected from the group consisting of cellulose polymer compounds, alginate, polysaccharides and acrylic acid polymers, preferably methyl cellulose compounds, ethyl cellulose compounds, hydroxyethylcellulose compounds, methylhydroxyethylcellulose compounds, methylhydroxypropylcellulose compounds, carboxymethyl cellulose compounds, alginic acids, sodium alginates, ammonium alginates, calcium alginates, gum arabic, guar gum or xanthan gum, or acrylic acid polymers with molecular weights from about 1,250,000 to 4,000,000, alone or in combination with each other. The polymers are used in a total concentration of 0.1 to 15%, preferably from 0.2 to 10%, and more preferably in an amount of from 0.5 to 7.5% by weight, calculated to total composition.

Composition can also comprise cationic polymers as conditioning and/or thickening agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-82, Quaternium-83 and Quaternium-84.

Compositions of the present invention can comprise an organopolysiloxane polymers wherein at least one silicium atom is linked to an alkylene group having a hetero-atom, in particular a nitrogen atom, with a poly-(N-acyl alkyleneimine) units of the formula $$-(CH_2)_n-\underset{\underset{R_9-C=O}{|}}{N}-$$

wherein n is a number from 1 to 5 and $R_9$ is hydrogen, a $C_1$-$C_{12}$-alkyl or cycloalkyl, aralkyl or aryl group. Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula $$CH_3-\underset{\underset{(CH_2)_x}{|}}{\overset{\overset{CH_3}{|}}{Si}O}-\underset{\underset{H_2N^\oplus\,\,Y^\ominus}{|}}{\overset{\overset{}{\phantom{|}}}{\phantom{Si}}}\Big]_m-\underset{\underset{CH_3}{|}}{\overset{\overset{CH_3}{|}}{SiO}}\Big]_n-\underset{\underset{CH_3}{|}}{\overset{\overset{CH_3}{|}}{Si}}-CH_3$$

$$H_2N^\oplus-\!\!\!-\!\!\![CH_2-CH_2-\underset{\underset{C_2H_5}{|}}{\overset{\overset{}{\phantom{|}}}{\underset{C=O}{N}}}\!\!]_y\!\!-R_{10},\quad Y^\ominus$$

wherein m and n each are numbers from 20 to 10,000, in particular 50 to 7,000, especially 100 to 5,000, x is a number between 1 and 5, preferably 3, and y is a number from 5 to 30, $R_{10}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Typical concentration range for any of the cationic polymers as conditioners mentioned above can be 0.1-7.5% by weight, preferably 0.3-5% by weight and more preferably 0.5-2.5% by weight, calculated to total composition Composition of the present invention may further comprise lipophilic ingredients such as vegetable oils, for example, marula oil, argan oil, shea butter oil, jojoba oil or any other; petrolatum liquid paraffins, especially paraffinum perliquidum and paraffinum subliquidum; silicone oils; hydropobic fatty acid esters such as octyl palmitate, isocetyl palmitate, isopropyl palmitate and octyl stearate, $C_{10}$- to $C_{36}$-fatty acid triglycerides, as well as their mixtures. In the case that the use is wished among those the most preferred ones are silicone oils, jojoba oil, fatty acid esters, paraffin oils, combinations of fatty acid esters and paraffin oils. Fatty acid esters and/or paraffin oils and/or silicone oils are particularly preferred. Concentration of these lipophilic compounds are used in a total amount of about 0.1 to 20 percent by weight, preferably from 1 to 15 percent by weight, and more preferably from 2 to 10 percent by weight, calculated to total composition.

In principal any silicone oil is useful as a lipophilic compound. Preferred are arylated silicones as a lipophilic ingredient at a concentration range of 0.1 to 50%, preferably 0.5 to 40% more preferably 1 to 35% and most preferably 2.5 to 30% by weight calculated to total composition.

Another preferred compound in the composition of present invention especially in bleaching and/or highlighting composition and in dyeing composition is ceramide type of compounds according to general formula

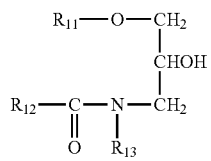

where $R_{11}$ and $R_{12}$ are independent from each other alkyl- or alkenyl group with 10 to 22 carbon atoms, $R_{13}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide. Concentration of ceramide type of compounds ranges from 0.01 to 2%, preferably 0.01 to 1% yb weight calculated to total composition before mixing.

The compositions of the present invention can comprise of at least one ubiquinone of the formula (I)

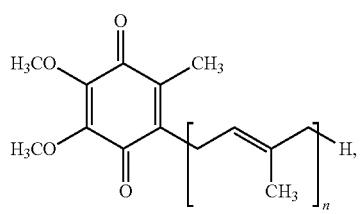

wherein n is a number from 1 to 10. Concentration of ubichinone can vary between 0.001% and 10% by weight, calculated to the total composition before mixing.

Compositions may further comprise additional substances found in coloring compositions for hair such as fragrance, humectants, chelants and radical scavengers.

Compositions of the present invention have a pH in the range of 2 to 12 and preferably 2.5 to 10.

Especially the alkaline compositions comprise at least one alkalizing agent especially when the pH is in the neutral to alkaline range. Suitable alkalizing agents are ammonia or ammonium hydroxide and a compound according to the general formula $$R_1R_2R_3N$$

wherein $R_1$, $R_2$ and $R_3$ are same or different H, C1-C6 alkyl, C1-C6 monohydroxyalkyl or C2-C6 polyhydroxyalkyl with the condition that at least one of $R_1$, $R_2$ and $R_3$ is a mono or polyhydroxyalkyl. Preferably $R_1$, $R_2$ and $R_3$ are same or different H, C1-C4 alkyl, C1-C4 monohydroxyalkyl or C2-C4 polyhydroxyalkyl with the condition that at least one of $R_1$, $R_2$ and $R_3$ is a mono or polyhydroxyalkyl.

Suitable alkanolamines according to the general formula of above are monoethanolamine, diethanolamine, triethanolamine, monoethanol methylamine, monoethanoldimethylamine, di-ethanolmethylamine, monoethanolethylamine, monoethanoldiethylamine, diethanolethylamine, monoethanolpropylamine, monoethanoldipropylamine, diethanolpropylamine, monoethanolbutylamine and diethanolbutylamine.

Preferred are monoethanolamine, diethanolamine and triethanolamine. The most preferred is monoethanolamine. Ammonia is also preferred as an alkalizing agent.

The concentration of at least one alkalizing agent varies between 1 and 35%, preferably 1 and 30, more preferably 2.5 and 25 and most preferably 2.5 to 20% by weight calculated to the total composition.

Composition of the present invention can comprise at least one oxidizing agent when lightening and coloring is carried out at the same process. The oxidizing agents suitable are hydrogen peroxide, urea peroxide, melamin peroxide or perborate salts. The preferred oxidizing agent is hydrogen peroxide, at a concentration in a range of 2 to 12% by weight calculated to the total composition.

The compositions of the present invention can additionally comprise at least one oxidizable solvent. With the term oxidizable it is meant that the solvent is oxidized, at least partly, which may also be as a whole under the conditions used for bleaching and colouring hair.

Suitable solvents are aromatic or aliphatic alcohols and preferably comprise only one OH group in its molecule. Preferably the aromatic alcohols have a LogP value (octanol water partition coefficient) at 25° C. in the range of 0 to 2.5, preferably in the range of 0.05 to 2, more preferably 1 to 2 and most preferably 1.1 to 1.7. Suitable aromatic oxidizable alcohols are 2-phenoxyethanol, benzyl alcohol, 2-phenylethanol and 2-benzyloxyethanol. Suitable aliphatic alcohols are isopropanol, propanol, n-butanol, isobutanol, t-butanol and 1-pentanol.

Most preferred oxidizable organic alcohols are the aromatic alcohols and among the aromatic oxidizable solvents benzyl alcohol, 2-phenoxyethanol, 2-phenylethanol are most preferred ones. Particularly preferred is benzyl alcohol.

At least one oxidizable solvent is comprise in the composition of the present invention is at a concentration below 8%, preferably 0.5 to 7.5% and more preferably 1 to 6% and most preferably 1 to 5% by weight calculate to the total composition.

The invention is illustrated with the following examples but not limited to.

EXAMPLE 1

|  | % by weight |
| --- | --- |
| Basic red 51 | 0.5 |
| Sodium lauryl glucose carboxylate* | 2.0 (active matter) |
| Lauryl glucoside | 1.5 (active matter) |
| Citric acid/sodium hydroxide | q.s. to pH 5.0 |
| Water | to 100 |

*Plantapon LGC Sorb was used.

For comparative purpose, the same composition as above was produced only with lauryl glucoside but not comprising any sodium lauryl glucose carboxylate. The sodium lauryl glucose carboxylate content was replaced with water.

Colouring was carried out by dipping human hair tresses into the solutions of inventive and comparative compositions and after processing of 20 min the tresses were taken out and rinsed off with water. It was observed that colour intensity of both tresses were comparable.

The coloured tresses were washed with commercially available shampoo composition under the brand Goldwell and designed for coloured hair for 6 times and that tresses were evaluated by naked eye for their colour intensity. It was observed the tress coloured with inventive composition was clearly darker red coloured than the tress coloured with comparative composition.

Similar results were observed with the following examples

EXAMPLE 2

|  | % by weight |
| --- | --- |
| Basic red 51 | 0.2 |
| Basic orange 31 | 0.1 |
| Basic yellow 87 | 0.05 |
| Sodium lauryl glucose carboxylate* | 2.0 (active matter) |
| Lauryl glucoside | 1.5 (active matter) |
| Cetearyl alcohol | 5.0 |
| Ceteareth-20 | 1.0 |
| Citric acid/sodium hydroxide | q.s. to pH 5.0 |
| Water | to 100 |

*Plantapon LGC Sorb was used.

EXAMPLE 3

|  | % by weight |
| --- | --- |
| Basic red 51 | 0.2 |
| HC red 3 | 0.3 |
| Sodium lauryl glucose carboxylate* | 1.0 (active matter) |
| Lauryl glucoside | 0.75 (active matter) |
| Cetearyl alcohol | 4.0 |
| Ceteareth-20 | 1.2 |
| Polyquaternium-10 | 0.5 |
| Citric acid/sodium hydroxide | q.s. to pH 5.5 |
| Water | to 100 |

*Plantapon LGC Sorb was used.

EXAMPLE 4

|  | % by weight |
| --- | --- |
| 2-Amino-6-chloro-4-nitrophenol | 0.5 |
| HC red 3 | 0.3 |
| Sodium lauryl glucose carboxylate* | 2.0 (active matter) |
| Lauryl glucoside | 1.5 (active matter) |
| Cetearyl alcohol | 5.0 |
| Ceteareth-20 | 1.0 |
| Polyquaternium-10 | 0.5 |
| Citric acid/sodium hydroxide | q.s. to pH 5.5 |
| Water | to 100 |

*Plantapon LGC Sorb was used.

EXAMPLE 5

|  | % by weight |
| --- | --- |
| 4-Hydroxypropylamino-3-nitrophenol | 3.0 |
| 2-Amino-6-chloro-4-nitrophenol | 0.8 |
| HC red 3 | 0.3 |
| Sodium lauryl glucose carboxylate* | 2.0 (active matter) |
| Lauryl glucoside | 1.5 (active matter) |
| Cetearyl alcohol | 9.0 |
| Ceteareth-20 | 2.0 |
| Cocamide-MEA | 5.6 |
| Sodium cetearyl sulphate | 3.0 |
| Ammonium hydroxide (25%) | 8.0 |
| Water | to 100 |

*Plantapon LGC Sorb was used.

As a comparative composition the same composition without sodium lauryl glucose carboxylate, but with 3.5% by weight lauryl glucoside was produced.

The above composition and the comparative composition were mixed with an oxidizing composition comprising 12% hydrogen peroxide at a weight ratio of 1:1 and applied onto hair and after processing 30 min at 40° C. rinsed off from hair and after drying the tresses were washed with commercially available shampoo composition for 6 times and afterwards the ΔE values were compared between inventive and comparative compositions. The following results were obtained.

|  | ΔE |
| --- | --- |
| Inventive composition | 3.5 |
| Comparative composition | 6.7 |

From the above result it is clear that the presence of sodium lauryl glucose carboxylate improve wash fastness of hair color.

The invention claimed is:
1. An aqueous hair dyeing composition comprising one or more hair direct dyes, at least one nonionic surfactant and at least one anionic sugar surfactant, wherein the at least one nonionic surfactant comprises an alky polyglucoside with an alkyl group of 8 to 18 carbon atoms and with 1 to 5 glucoside units and is present at a concentration in the range of 0.1 to 20% by weight calculated to the total composition, wherein the at least one anionic sugar surfactant comprises lauryl glucose carboxylate and/ or its alkali metal salt and is present at a concentration in the range of 0.1 to 25% by weight calculated to the total composition.

2. The composition according to claim 1 wherein the one or more hair direct dyes are selected from anionic, cationic and neutral nitro dyes.

3. The composition according to claim 2 wherein the one or more direct dyes is a cationic dyes selected from the group consisting of Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic red 51, Basic Yellow 87 and Basic Orange 31.

4. The composition according to claim 2 wherein the one or more direct dyes is an anionic dye selected from the group consisting of Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts.

5. The composition according to claim 2 wherein the one or more direct dyes is a neutral nitro dyes selected from the group consisting of HC Blue No.2, HC Blue No.4, HC Blue No.5, HC Blue No.6, HC Blue No.7, HC Blue No.8, HC Blue No.9, HC Blue No.10, HC Blue No.11, HC Blue No.12, HC Blue No.13, HC Brown No.1, HC Brown No.2, HC Green No.1, HC Orange No.1, HC Orange No.2, HC Orange No.3, HC Orange No.5, HC Red BN, HC Red No.1, HC Red No.3, HC Red No.7, HC Red No.8, HC Red No.9, HC Red No.10, HC Red No.11, HC Red No.13, HC Red No.54, HC Red No.14, HC Violet BS, HC Violet No.1, HC Violet No.2, HC Yellow No.2, HC Yellow No.4, HC Yellow No.5, HC Yellow No.6, HC Yellow No.7, HC Yellow No.8, HC Yellow No.9, HC Yellow No.10, HC Yellow No.11, HC Yellow No.12, HC Yellow No.13, HC Yellow No.14, HC Yellow No.15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

6. The composition according to claim 1 wherein the composition is an emulsion and further comprises fatty alcohol.

7. The composition according to claim 1 further comprising a cationic polymer.

8. The composition according to claim 1 further comprising at least one oxidizing agent.

9. The composition according to claim 1 further comprising at least one alkalizing agent selected from ammonia or ammonium hydroxide and a compound according to the general formula

wherein R1, R2 and R3 are same or different H, C1-C6 alkyl, C1-C6 monohydroxyalkyl or C2 - C6 polyhydroxyalkyl with the condition that at least one of R1, R2 and R3 is a mono or polyhydroxyalkyl.

10. A process for coloring hair comprising applying the composition according to claim 1 onto hair, processing the composition on the hair for 1 to 45 min, and rinsing the composition from the hair.

11. An aqueous hair dyeing composition comprising one or more hair direct dyes selected from the group consisting cationic dyes and neutral nitro dyes, at least one nonionic surfactant and at least one anionic sugar surfactant, wherein the at least one nonionic surfactant comprises an alky polyglucoside with an alkyl group of 8 to 18 carbon atoms and with 1 to 5 glucoside units, where the at least one anionic sugar surfactant comprises lauryl glucose carboxylate and/or its alkali metal salt.

12. The composition according to claim 1, wherein the at least one nonionic surfactant is present at a concentration in the range of 0.2 to 10% by weight, calculated to the total composition and the at least one anionic sugar surfactant is present at a concentration in the range of 1 to 10% by weight, calculated to the total composition.

13. The composition according to claim 12, wherein the at least one nonionic surfactant comprises lauryl glucoside and the at least one anionic sugar surfactant comprises sodium lauryl glucose carboxylate.

14. The composition according to claim 1, wherein the at least one anionic sugar surfactant comprises lauryl glucose carboxylate and/ or its alkali metal salt and is present at a concentration in the range of 1 to 10% by weight calculated to the total composition.

* * * * *